United States Patent [19]

Kay

[11] 3,959,469

[45] May 25, 1976

[54] TRIAZINEDIONE COMPOUNDS AS FUNGICIDAL AND BACTERICIDAL AGENTS

[75] Inventor: Ian Trevor Kay, Wokingham, England

[73] Assignee: Imperial Chemical Industries Limited, London, England

[22] Filed: Feb. 3, 1975

[21] Appl. No.: 546,318

[30] Foreign Application Priority Data

Feb. 15, 1974 United Kingdom............... 43514/74

[52] U.S. Cl. .............................................. 424/249
[51] Int. Cl.² .......................................... A01N 9/22
[58] Field of Search................... 424/249; 260/249.5

[56] References Cited
UNITED STATES PATENTS 3,850,924  11/1974  Fuchs et al. ..................... 260/249.5

Primary Examiner—Sam Rosen
Assistant Examiner—Allen J. Robinson
Attorney, Agent, or Firm—Cushman, Darby & Cushman

[57] ABSTRACT

Plant fungicidal and bactericidal compositions containing a triazinedione of the formula:

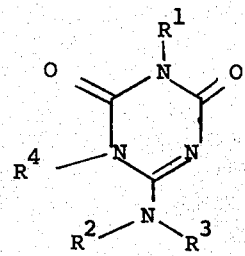

wherein $R^1$ is alkyl, alkenyl, cycloalkyl, phenyl, halophenyl or adamantyl; $R^2$ is alkyl or together with $R^3$ and the nitrogen atom to which they are attached form a pyrrolidine ring; $R^3$ is hydrogen, alkyl, alkoxy, phenyl or amino; $R^4$ is hydrogen or alkyl; or a salt thereof; and the processes for combating plant fungi and bacteria using them.

2 Claims, No Drawings

TRIAZINEDIONE COMPOUNDS AS FUNGICIDAL AND BACTERICIDAL AGENTS

This invention relates to a method of combating fungal and bacterial infections of plants by the use of certain triazine derivatives; and to plant anti-fungal and anti-bacterial compositions; and to certain novel, specific, triazine derivatives.

The present invention provides a process for combating fungal and bacterial diseases of plants which comprises applying to plants or to the locus of plants, a fungicidally or bactericidally effective, but non-phytotoxic, amount of a triazine derivative of the general formula:

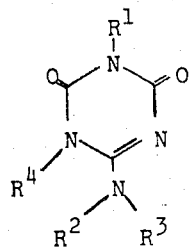

Wherein $R^1$ is alkyl, alkenyl, cycloalkyl, phenyl, halophenyl or adamantyl; $R^2$ is alkyl or together with $R^3$ and the adjacent N- atom forms a pyrrolidine ring; $R^3$ is hydrogen, alkyl, alkoxy, phenyl or amino; and $R^4$ is hydrogen or alkyl; or a salt thereof.

Preferred compounds of the invention for use as plant fungicides and bactericides are those in which $R^1$ is an alkyl radical of from 1 to 6 carbon atoms or a cycloalkyl radical; $R^2$ is an alkyl radical of from 1 to 4 carbon atoms; $R^3$ is hydrogen, an alkyl radical of from 1 to 4 carbon atoms, an alkoxy radical of from 1 to 4 carbon atoms, phenyl or amino; and $R^4$ is hydrogen, or an alkyl radical of from 1 to 4 carbon atoms.

Even more preferred compounds are those wherein, in the general formula, $R^1$ is an alkyl radical of from 1 to 6 carbon atoms, or cycloalkyl; $R^2$ is an alkyl radical of from 1 to 4 carbon atoms; $R^3$ is hydrogen; and $R^4$ is hydrogen, or an alkyl radical of from 1 to 4 carbon atoms.

When $R^4$ is a hydrogen atom, the hydrogen is acidic, and the compounds will form salts with bases. Examples of such salts include alkali metal salts, for example lithium, sodium and potassium salts, alkaline earth metal salts, for example calcium and magnesium salts, ammonium salts, and salts formed from primary, secondary, or tertiary amines, for example primary, secondary and tertiary aliphatic amines in which the one, two or three aliphatic radicals each contain from one to six carbon atoms. Salts of compounds wherein $R^4$ represents a hydrogen atom may in general be conveniently prepared simply by mixing the triazinedione compound with the stoichiometric proportions of an alkali metal hydroxide, alkaline earth metal hydroxide, ammonia, or amine, in a solvent or diluent. Water is generally the most convenient solvent or diluent for this purpose.

In a further aspect the invention provides plant antifungal and anti-bacterial compositions comprising as an active ingredient a triazine derivative, or a salt thereof, as defined in any of the preceding paragraphs; together with a carrier for the active ingredient; and, optionally, a surface-active agent.

Particular examples of triazine derivatives useful in the practice of the invention are set forth in Table 1 below.

TABLE 1

The compounds of Table 1 have the general formula:

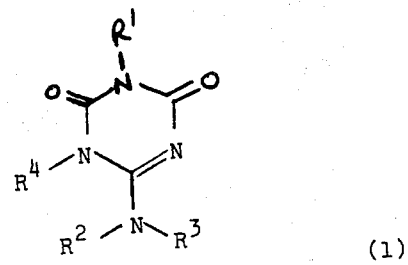

(1)

TABLE I

| COMPOUND No. | $R^1$ | $R^2$ | $R^3$ | $R^4$ | MELTING POINT |
|---|---|---|---|---|---|
| 1 | 4-Chlorophenyl | $CH_3$ | $CH_3$ | H | 264–266 |
| 2 | $C_2H_5$ | $CH_3$ | $CH_3$ | H | 236–238 |
| 3 | $n-C_4H_9$ | $CH_3$ | $CH_3$ | H | 184 |
| 4 | $C_2H_5$ | $C_2H_5$ | $C_2H_5$ | H | 202 |
| 5 | $n-C_4H_9$ | $C_2H_5$ | $C_2H_5$ | H | 127 |
| 6 | Cyclohexyl | $C_2H_5$ | $C_2H_5$ | H | 188–190 |
| 7 | $n-C_3H_7$ | $CH_3$ | $CH_3$ | H | 183 |
| 8 | Cyclohexyl | $CH_3$ | $CH_3$ | H | 270 |
| 9 | iso $C_3H_7$ | $CH_3$ | $CH_3$ | H | 216–217 |
| 10 | $t-C_4H_9$ | $CH_3$ | $CH_3$ | H | 201–203 (dec) |
| 11 | $-CH_2CH=CH_2$ | $CH_3$ | $CH_3$ | H | 187 |
| 12 | $n-C_4H_9$ | $C_2H_5$ | H | H | 244 |
| 13 | iso-$C_3H_7$ | 1-pyrrolidino | | H | 259–261 (dec) |
| 14 | cyclohexyl | 1-pyrrolidino | | H | 292–293 (dec) |
| 15 | iso-$C_3H_7$ | $CH_3$ | $C_2H_5$ | H | 161–162 |
| 16 | $n-C_6H_{13}$ | $CH_3$ | $CH_3$ | H | 168 |
| 17 | iso-$C_3H_7$ | $CH_3$ | $CH_3$ | H | 91–93 |
| 18 | iso-$C_3H_7$ | $CH_3$ | phenyl | H | 225–226 |
| 19 | cyclohexyl | $CH_3$ | H | H | 299–300 |
| 20 | $n-C_6H_{13}$ | $C_2H_5$ | H | H | 218–20 |
| 21 | $n-C_4H_9$ | $n-C_4H_9$ | H | H | 247–248 |
| 22 | $n-C_4H_9$ | $CH_3$ | H | H | 241–242 |
| 23 | $n-C_6H_{13}$ | $CH_3$ | H | H | 229–230 |
| 24 | $-\overset{CH_3}{\underset{\vert}{CH}}-CH_2-CH_3$ | $CH_3$ | $CH_3$ | H | 168–169 (dec) |
| 25 | $-CH(C_2H_5)_2$ | $CH_3$ | $CH_3$ | H | 162 (dec) |

TABLE I-continued

| COMPOUND No. | R¹ | R² | R³ | R⁴ | MELTING POINT |
|---|---|---|---|---|---|
| 26 | adamentyl | $CH_3$ | $CH_3$ | H | 219 (dec) |
| 27 | $-CH_2CH(CH_3)_2$ | $CH_3$ | $CH_3$ | H | 215 |
| 28 | iso-$C_3H_7$ | $CH_3$ | $NH_2$ | H | 196-197 |
| 29 | cyclohexyl | $C_2H_5$ | H | H | 258-259 (dec) |
| 30 | cyclohexyl | $CH_3$ | H | $CH_3$ | 262 |
| 31 | cyclohexyl | $C_2H_5$ | H | $CH_3$ | 214 |
| 32 | iso-$C_3H_7$ | $CH_3$ | H | $CH_3$ | 224 |
| 33 | iso-$C_3H_7$ | $CH_3$ | $OCH_3$ | H | 169-170 |
| 34 | cyclohexyl | $CH_3$ | $CH_3$ | $CH_3$ | 98 |
| 35 | n-$C_4H_9$ | n-$C_3H_7$ | n-$C_3H_7$ | H | 110 |
| 36 | n-$C_6H_{13}$ | $C_2H_5$ | $C_2H_5$ | H | 108-109 |
| 37 | n-$C_4H_9$ | pyrrolidinyl | | H | 226-227 |
| 38 | cyclohexyl | $CH_3$ | $NH_2$ | $CH_3$ | 172-174 |
| 39 | n-$C_8H_{17}$ | $CH_3$ | $CH_3$ | H | 150 |
| 40 | iso-$C_3H_7$ | $C_2H_5$ | H | H | 228 |

Some of the above listed derivatives are all novel.

In a yet further aspect, therefore, this invention includes the specific triazine derivatives set out in Table 1, herein above.

The compounds of formula 1 above, in general terms, may be prepared by methods described in copending U.K. application Nos. 50827/73 and 6959/74.

Thus, in one method, a guanidine derivative of formula

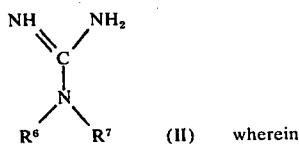

(II) wherein R⁶ and R⁷ may each be a hydrogen atom or an aliphatic radical, is reacted with a chloroformic ester $ClCO_2R^8$, wherein R⁸ is a hydrocarbyl group, preferably an alkyl group of 1 to 6 carbon atoms, for example methyl or ethyl, or preferably with a dialkylcarbonate $(R^8O)_2CO$ to give an intermediate (III). This is then further reacted with an isocyanate $R^1NCO$ wherein R¹ has any of the meanings hereinbefore assigned to it. The reaction product so obtained cyclises to a triazinedione compound, as shown in the scheme below:

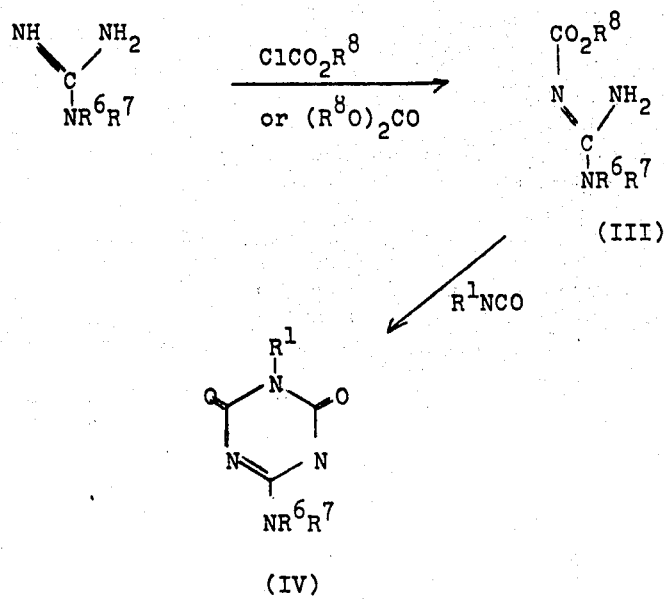

The conversion of (III) to (IV) may be carried out in the presence of a catalytic amount of a tertiary amine, preferably a trialkylamine in which each of the three alkyl groups contains 1 to 6 carbon atoms.

The reaction of the chloroformic ester $ClCO_2R^8$ with the guanidine may be carried out in water. Alternatively the preparation of the ethoxycarbonyl guanidine may be carried out by reacting diethylcarbonate with the free guanidine base in ethanol solution. In this method the free guanidine is preferably prepared in ethanol by adding 1 molar proportion of sodium ethoxide to a guanidine salt in ethanol.

Especially preferred compounds include those numbered 30 and 40 in Table I above.

In fungicide tests compound number 40 of Table 1 gave good control of Wheat Rust, *Puccinia recondita* at an application rate of 50 parts per million, both in an eradicant, and in a protectant test.

Compound No. 30 of Table I gave good control at the low application rate of 3 parts per million is a translocation (systemic) test (that is a test in which the soil surrounding the roots of the plants was drenched with a solution of the compound) against the oat Rust *Puccinia hordei* and against Crown Rust of oats *Puccinia coronata*. Against Wheat Rust, *Puccinia recondita*, this compound also gave good disease control at the low application rate of 5 parts per million.

The triazine derivatives may be used as fungicides or bactericides alone, but are preferably incorporated in a composition comprising a diluent in addition to the triazine derivative; and may be used for agricultural and herbicidal purposes. The triazine derivatives and compositions containing them, are variously active against a variety of fungal pathogens of plants and seeds including, for example, the following:

| *Erysiphe graminis* | (Powdery Mildew) | on barley |
| *Puccinia recondita* | (Rust) | on wheat |
| *Puccinia hordei* | (Rust) | on oats |
| *Pytophthora infestans* | (Late Blight) | on tomatoes |
| *Puccinia coronata* | (Brown Rust) | on oats |
| *Plasmopara viticola* | (Downy Mildew) | on vines |
| *Uncinula necator* | (Powdery Mildew) | on vines |
| *Podosphaera leucotricha* | (Powdery Mildew) | on apples |

The triazine compounds, and compositions containing them, are also variously active against a variety of foliage-borne bacterial plant diseases, including for example, the following:

| *Xanthomonas oryzae* | (bacterial blight of rice) |
| *Erwinia amylovora* | (fireblight of pears) |
| *Pseudomonas tomato* | (bacterial speck of tomato) |
| *Xanthomonas vesicatoria* | (bacterial spot of peppers) |
| *Pseudomonas tabaci* | (wildfire of tobacco) |

For the control of both fungal and bacterial infections of plants the rate at which the triazine compounds of the invention are applied will vary, depending upon the particular compound chosen for use, the disease to be controlled and on the particular species of plant acting as host to the disease. However, a non-phytotoxic rate of application is necessary, as exemplified, hereinafter, with specific reference to Examples 11 and 12.

In carrying the invention process into practical effect the growing crops, plants, seeds, or soil may be treated by any of the well-known and established procedures used in agriculture and crop protection. Thus, for example, the active compound may be applied as solids, liquids, solutions, dispersions, emulsions and these may comprise, in addition to the active substance, any other adjuvant useful for formulation purposes, or any other biologically active substance, for example to increase the number of diseases combated.

Such solid or liquid substances and formulations may be applied, for example, by any conventional technique, for example, by dusting, or otherwise applying the solid substances and formulations to the surfaces of growing crops, harvested produce, plants, seeds or soil, or to any part, or combination of parts thereof, or, for example, applying liquids or solutions for example, by dipping, spraying, mist-blowing or soaking techniques.

The invention process is therefore useful for treating plants, seeds, harvested fruits, vegetables, or cut flowers infested with, or liable to infestation with any of the aforementioned specific fungal or bacterial diseases.

The term "seeds" is intended to include propagative plant forms generally and therefore includes, for example, cut stems, corms, tubers, rhizomes and the like.

As previously noted the triazine compounds are preferably used in admixture with a solid or liquid diluent. The admixtures so obtained are hereinafter referred to as compositions. Preferably the compositions comprise a surface-active agent.

The solid compositions may be, for example, in the form of dusting powders, or may take the form of granules. Suitable solid diluents include, for example, kaolin, bentonite, kieselguhr, dolomite, calcium carbonate, talc, powdered magnesia and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface-active agents. Water or organic liquids may be used to prepare solutions, dispersions, or emulsions of the active ingredient. The liquid compositions of the invention may also contain one or more corrosion inhibitors for example, lauryl isoquinolinium bromide.

Surface-active agents may be of the cationic, anionic or non-ionic type. Suitable agents of the cationic type include, for example, cetyltrimethyl ammonium bromide. Suitable agents of the anionic type include, for example, soaps, salts of aliphatic monoesters of sulphuric acid, for example, sodium lauryl sulphate; and salts of sulphonated aromatic compounds, for example, dodecylbenzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol and octylcresol. Other non-ionic agents are the partial esters derived from long chain fatty acids and hexitol anhydrides, for example, sorbitol monolaurate, and the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment. In general concentrates may conveniently contain from 10 to 85% and preferably from 25 to 60% by weight of active ingredient. A particularly preferred form of concentrate is an emulsifiable concentrate comprising a solution of a triazine derivative, as defined above, in an organic solvent containing a surface-active agent. When required for use, the concentrate can readily be dispersed in water by agitation to provide a dilute emulsion suitable for spraying. Dilute preparations ready for use may contain varying amounts of the active ingredient, depending upon the purpose for which they are to be used; however, dilute preparations may contain between 0.0005 and 0.1% by weight of the active ingredient.

It is to be understood that the fungicidal compositions used in this invention may comprise, in addition to one or more triazine derivatives, one or more other compounds having biological activity.

The invention is illustrated, but not limited, by the following Examples.

EXAMPLE 1

This example illustrates the preparation of compounds according to the invention and as listed in Table I.

a. Preparation of carbamate intermediate

N,N-dimethylguanidine hydrochloride (123.5 g; 1M) was added to a solution of potassium hydroxide (112.2 g; 2M) in water (ca. 300 ml.). The solution was stirred and kept at −10° to −5°C by cooling while ethyl chloroformate (108.5 g; 1M) was added over a period of 45 minutes. After addition was complete, the solution was allowed to warm to room temperature, the water was evaporated in a vacuum, and the residue was extracted with boiling chloroform (300ml.). The extracts were cooled, dried, and evaporated to yield a yellow oily solid. Recrystallisation from a 2:1 mixture of toluene and petroleum (b.p. 40°–60°C) gave the white crystalline carbamate derivative (formula III, $R^8=C_2H_5$, $R^6=R^7=CH_3$) having a melting point of 73°–76°C.

b. Preparation of triazinedione

The carbamate derivative so obtained was dissolved in dry toluene (ca. 100ml. per 15 g. of carbamate) and heated under reflux with ethyl isocyanate (1 molar proportion) and a little dry triethylamine as catalyst for 16 hours. The toluene was then removed in a vacuum and the residue recrystallised from ethanol, giving the triazine dione as a white fibrous solid of melting point 236°–238°C.

Using the appropriate guanidine starting material and aliphatic isocyanate the following 4-aminotriazinediones (Table II below) were prepared by the above procedure.

TABLE II

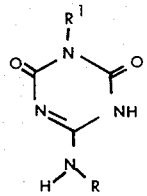

| $R^1$ | R | MELTING POINT °C |
|---|---|---|
| $C_4H_9$ | $C_2H_5$ | 244 |
| iso $C_3H_7$ | $C_2H_5$ | 228 |
| iso $C_3H_7$ | $CH_3$ | 280–282 |

TABLE II-continued

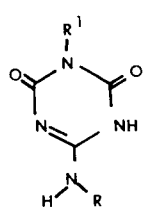

| $R^1$ | R | MELTING POINT °C |
|---|---|---|
| n hexyl | $C_2H_5$ | 218–220 |
| n $C_4H_9$ | n $C_4H_9$ | 247–248 |
| iso $C_3H_7$ | iso $C_3H_7$ | 235–237 |
| n $C_4H_9$ | $CH_3$ | 241–242 |

EXAMPLE 2

An emulsifiable concentrate was made up by mixing together the ingredients set out below in the proportions stated and stirring the mixture until all the constituents were dissolved.

| Compound No. 30 of Table I | 10% |
|---|---|
| Ethylene Dichloride | 40% |
| Calcium dodecylbenzene-sulphonate | 5% |
| "Lubrol" L | 10% |
| "Aromasol" H | 35% |

EXAMPLE 3

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44–100, to obtain the desired size of grains.

| Compound No. 40 (Table I) | 50% |
|---|---|
| "Dispersol" T | 25% |
| "Lubrol" APN 5 | 1.5% |
| Sodium Acetate | 23.5% |

EXAMPLE 4

The ingredients listed below were all ground together in the proportions stated to produce a powder formulation readily dispersible in liquids.

| Compound No. 30 (Table I) | 45% |
|---|---|
| "Dispersol" T | 5% |
| "Lissapol" NX | 0.5% |
| "Cellofas" B600 | 2% |
| Sodium acetate | 47.5% |

EXAMPLE 5

The active ingredient (Compound No. 40 of Table I) was dissolved in a solvent and the resultant liquid was sprayed on to the granules of Fuller's earth. The solvent was then allowed to evaporate to produce a granular composition.

| Compound No. 40 (Table I) | 5% |
|---|---|
| Fuller's earth or | |
| China clay granules | 95% |

EXAMPLE 6

A dusting powder was prepared by mixing, in the proportions stated, the active ingredient with talc.

| Compound No. 30 (Table I) | 5% |
|---|---|
| Talc | 95% |

EXAMPLE 7

A Col formulation was prepared by ball-milling the constituents set out below and then forming an aqueous suspension of the ground mixture with water.

| Compound No. 40 (Table I) | 40% |
|---|---|
| "Dispersol" | 10% |
| "Lubrol" | 1% |
| Water | 49% |

EXAMPLE 8

A dispersible powder formulation was made by mixing together the ingredients set out below and then grinding the mixture until all the constituents were thoroughly mixed.

| Compound No. 30 of Table I | 25% |
|---|---|
| "Aerosol" OT/B | 2% |
| "Dispersol" A.c. | 5% |
| China Clay | 28% |
| Silica | 40% |

EXAMPLE 9

This example illustrates the preparation of two dispersible powder formulations. In each instance all the ingredients are mixed in the proportions stated and the mixture then ground in a comminution mill.

| Compound No. 40 of Table I | 25% |
|---|---|
| "PERMINAL" BX | 1% |
| "Dispersol" T | 5% |
| Polyvinylprrolidone | 10% |
| Silica | 25% |
| China clay | 34% |

Exactly the same formulation was made using Compound No 30 of Table I.

EXAMPLE 10

The ingredients set out below were formulated into a dispersible powder by mixing and grinding the ingredients in the proportions stated.

| Compound No. 40 of Table | 25% |
|---|---|
| "AEROSOL" OT/B | 2% |

| "Dispersol" A | 5% |
|---|---|
| China Clay | 68% |

Exactly the same formulation was prepared using Compound No. 30 of Table I instead of Compound No. 40.

In Examples 2–10 above percentage amounts are on a weight basis.

The following constitutes an explanation of the compositions or substances represented by the various Trade Marks and Trade Names referred to in the foregoing Examples.

"LUBROL" L is a condensate of 1 mole of nonyl phenol with 13 molar proportions of ethylene oxide.

"AROMASOL" H is a solvent mixture of alkylbenzenes

"DISPERSOL" T AND AC is a mixture of sodium sulphate and a condensate of formaldehyde with the sodium salt of naphthalene sulphonic acid.

"LUBROL" APN 5 is a condensate of 1 mole of nonyl phenol with 5½ moles of naphthalene oxide.

"CELLOFAS" B 600 is a sodium carboxymethyl cellulose thickener.

"LISSAPOL" NX is a condensate of 1 mole of nonyl phenol with 8 moles of ethylene oxide.

"AEROSOL" OT/B is dioctyl sodium sulphosuccinate.

"PERMINAL" BX is an alkyl naphthalene sulphonate (sodium salt)

EXAMPLE 11

The triazine derivatives were tested against a wide variety of foliar fungal diseases of plants. In the test, a composition comprising an aqueous solution or suspension of the test compound was sprayed on to the foliage of uninfected plants; the soil in which the plants were growing was also drenched with the composition. The compositions used for spraying and drenching contained 100 parts per million (ppm.) (unless otherwise expressly stated) of the test compound. After spraying and drenching, the plants were then exposed to infection with the diseases it was desired to control, along with control plants not treated with the compound. After a period of days, depending upon the particular disease, the extent of the disease was visually assessed, as a percentage of the disease established upon the control plants which had not been treated with the compound under test, according to the grading scheme below.

| Grading | Amount of disease as a percentage of disease on control plants |
|---|---|
| 0 | 61 to 100 |
| 1 | 26 to 60 |
| 2 | 6 to 25 |
| 3 | 0 to 5 |
| 4 | No disease |

In Table III and Table V below the names of the diseases are given in the first column, and in the second column is given the time which elapsed between exposing the plants to infection and assessing the amount of disease. Tables IV and VI give the test results.

TABLE III

| DISEASE AND PLANT | TIME INTERVAL (DAYS) | DISEASE CODE LETTER (TABLE IV) |
|---|---|---|
| PLASMOPARA VITICOLA (Vine) | 7 | A |
| UNCINULA NECATOR (Vine) | 10 | B |
| PODOSPHAERA LEUCOTRICHA (Apple) | 10 | C |

TABLE IV

| COMPOUND NO. (TABLE I) | DISEASE CODE LETTER | | |
|---|---|---|---|
| | A | B | C |
| 5 | P | 3 | 3 |
| 6 | 3 | 3 | 3 |
| 7 | 3 | 3 | — |
| 9 | 3 | P | 3 |
| 10 | 3 | P | P |
| 12 | 0 | 3 | 3 |
| 13 | 3 | 3 | P |
| 15 | 4 | 3 | 4 |
| 16 | 2 | 3 | 0 |
| 20 | 0 | 3 | 4 |
| 21 | 0 | 3 | 3 |
| 22 | 0 | 4 | 4 |
| 34 | 4 | 3 | P |
| 35 | 0 | 4 | 3 |
| 37 | P | 4 | 0 |
| 38 | 4 | 3 | 3 |
| 39 | 3 | 2 | — |
| 40 | 3 | 3 | 0 |

"P" denotes too much phytotoxicity to get a meaningful assessment of anti-fungal activity
"—" denotes not tested.

TABLE V

| DISEASE AND PLANT | TIME INTERVAL (DAYS) | DISEASE CODE LETTER (TABLE VI) |
|---|---|---|
| Puccinia recondita (wheat) | 10 | D |
| ERYSIPHE GRAMINIS (Barley) | 10 | E |

TABLE VI

| COMPOUND NO. (TABLE I) | DISEASE CODE LETTERS | |
|---|---|---|
| | D APPLICATION RATE OF 100 ppm | E APPLICATION RATE OF 100 ppm |
| 1 | 3 | — |
| 2 | 3 | 0 |
| 4 | 3 | 0 |
| 6 | 3 | — |
| 22 | 0 | 3 |
| | | APPLICATION RATE of 50 ppm |
| 9 | 3 | 2 |
| 10 | 3 | 1 |
| 13 | P | 4 |
| 14 | P | 3 |
| 15 | 3 | 1 |
| 16 | 0 | 4 |
| 17 | 3 | — |
| 18 | 3 | 0 |
| 20 | 0 | 4 |
| 21 | 0 | 3 |
| 23 | 0 | 4 |
| 24 | 3 | 4 |
| 25 | 3 | 2 |
| 26 | 0 | 3 |
| 27 | 3 | 2 |
| 27 | 3 | 2 |
| 28 | 3 | 4 |
| 29 | 3 | 2 |
| 30 | 3 | 1 |
| 31 | 3 | 1 |
| 32 | 3 | 1 |
| 34 | 3 | P |
| 37 | 3 | 1 |
| 38 | 1 | 3 |
| 3 | 3 | 3 |
| 7 | 0 | 2 |
| 11 | 1 | 1 |
| 12 | 0 | 4 |
| 19 | 4 | 1 |
| 20 | 0 | 4 |
| 33 | 3 | 4 |
| 35 | 1 | 4 |
| 36 | 0 | 4 |
| 5 | P | 4 |
| 8 | 3 | 3 |

(Results below are at an application rate of 25 ppm for rows 3 through 8)

EXAMPLE 12

The triazine compounds were tested against a variety of foliage-borne bacterial plant diseases in the glasshouse. The anti-bacterial screening method employed a mist propagator to aid infection of treated plants by providing conditions of high humidity.

The plants were sprayed and/or root drenched with an aqueous solution containing various concentrations of the test chemical. After 48 hours they were inoculated with the appropriate disease organism. Inoculations were accompanied by wounding the plants, which was necessary for bacterial infection to take place. Immediately afterwards the plants were placed under high humidity. Agrimycin (17% Streptomycin sulphate) at 2000 ppm and 1000 ppm. was applied as a standard treatment and with water as a control. After 8 days, the symptoms were assessed on a 0–4 scale given in Table VII below, wherein the extent of the disease is given in the form of a grading as follows:

| Grading | Percentage Amount of Disease |
|---|---|
| 0 | 61 – 100 |
| 1 | 26 – 60 |
| 2 | 6 – 25 |
| 3 | 0 – 5 |
| 4 | No disease | and the disease code of the Table VII is given below:

| Disease and Plant | Disease Code |
|---|---|
| Xanthomonas oryzae (bacterial blight of rice) | A |
| Erwinia amylovora (fireblight on pears) | B |
| Pseudomonas tomato (bacterial speck of tomato) | C |

TABLE VII

| COMPOUND NO. TABLE I | RATE OF APPLICATION (ppm) | DISEASE CODE | | | |
|---|---|---|---|---|---|
| | | A | B | C | |
| 4 | 200 | 1 | 0 | 2 | R/S |
| 11 | 200 | 2 | 0 | 3 | R/S |
| 20 | 200 | 3 | 0 | 3 | R/S |
| 18 | 100 | 1 | 3 | — | R/S |
| 2 | 100 | 3 | 0 | 3 | R and S |
| 7 | 50 | 2* | 3 | 3 | R and S |

R/S denotes a combined root drench ad foliar spray test.
R and S denote individual root drench and foliar spray tests.
*denotes a result obtained by a foliar spray test alone.

I claim:

1. A process for combating fungi or bacteria on plants which comprises applying to said fungi or bacteria, a fungicidally or bactericidally effective, but non-phytotoxic, amount of a triazine derivative of the formula:

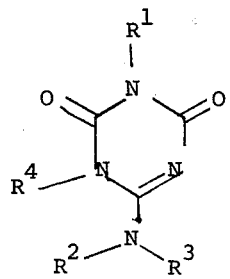

wherein $R^1$ is alkyl of from 1 to 8 carbon atoms, allyl, adamentyl, chlorophenyl, or cyclohexyl; $R^2$ is alkyl of from 1 to 4 carbon atoms or toether with $R^3$ and the adjacent N-atom forms a pyrrolidine ring; $R^3$ is hydrogen, alkyl of from 1 to 4 carbon atoms, alkoxy of from 1 to 4 carbon atoms, phenyl or amino; and $R^4$ is hydrogen or alkyl of from 1 to 4 carbon atoms; or alkali metal, alkaline earth metal, ammonium or amine salt.

2. The process according to claim 1 wherein $R^1$ is alkyl of from 1 to 6 carbon atoms, or cyclohexyl; $R^2$ is alkyl of from 1 to 4 carbon atoms; $R^3$ is hydrogen; and $R^4$ is hydrogen, or alkyl of from 1 to 4 carbon atoms.

\* \* \* \* \*